United States Patent
Charles

(10) Patent No.: US 11,564,711 B2
(45) Date of Patent: Jan. 31, 2023

(54) ADJUSTABLE LENGTH INFUSION CANNULA

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 293 days.

(21) Appl. No.: 16/829,268

(22) Filed: Mar. 25, 2020

(65) Prior Publication Data

US 2020/0337722 A1 Oct. 29, 2020

Related U.S. Application Data

(60) Provisional application No. 62/838,612, filed on Apr. 25, 2019.

(51) Int. Cl.
*A61B 17/34* (2006.01)
*A61F 9/00* (2006.01)
*A61B 17/00* (2006.01)

(52) U.S. Cl.
CPC ........ *A61B 17/3423* (2013.01); *A61F 9/0017* (2013.01); *A61B 2017/00862* (2013.01); *A61B 2017/00991* (2013.01); *A61B 2017/347* (2013.01)

(58) Field of Classification Search
CPC ............ A61M 25/02; A61M 2025/024; A61B 17/3423; A61B 2017/3443; A61B 2017/349; A61B 2017/3492
See application file for complete search history.

(56) References Cited

U.S. PATENT DOCUMENTS

| | | | |
|---|---|---|---|
| 4,593,681 A | * | 6/1986 | Soni ............... A61B 17/320016 |
| | | | 600/102 |
| 7,783,346 B2 | | 8/2010 | Smith et al. |
| 8,062,260 B2 | | 11/2011 | Mccawley |
| 8,062,305 B2 | | 11/2011 | Wenchell |
| 8,092,423 B2 | | 1/2012 | Gresham |
| 8,251,980 B2 | | 8/2012 | Zica |
| 8,771,223 B2 | * | 7/2014 | Patton ................ A61B 17/3421 |
| | | | 604/93.01 |
| 8,961,548 B2 | * | 2/2015 | Buser ..................... A61B 90/30 |
| | | | 606/174 |
| 9,089,364 B2 | | 7/2015 | Bhadri |
| 9,198,797 B2 | | 12/2015 | Kerns |
| 9,730,834 B2 | | 8/2017 | Charles |
| 9,999,542 B2 | | 6/2018 | Humayun |
| 10,610,408 B2 | | 4/2020 | Farley |
| 2008/0097346 A1 | | 4/2008 | Charles |
| 2008/0125712 A1 | | 5/2008 | Dacquay |

(Continued)

*Primary Examiner* — Laura A Bouchelle

(74) *Attorney, Agent, or Firm* — Patterson + Sheridan, LLP

(57) ABSTRACT

Certain embodiments provide an adjustable length infusion cannula having a cannula including a first proximal end and a first distal end, and a hub having a second proximal end, a second distal end, and a central aperture that extends between the second proximal end and the second distal end. The central aperture is configured to accept the first distal end of the cannula and allow the cannula upward movement and downward movement through the hub. The adjustable length infusion cannula also includes a locking mechanism configured to lock the cannula within the hub such that the first distal end extends a first distance past the second distal end of the hub.

2 Claims, 7 Drawing Sheets

(56) References Cited

U.S. PATENT DOCUMENTS

| | | |
|---|---|---|
| 2008/0172009 A1 | 7/2008 | Attinger |
| 2008/0177239 A1 | 7/2008 | Li |
| 2009/0076463 A1 | 3/2009 | Attinger |
| 2016/0067083 A1 | 3/2016 | Lue |
| 2016/0106461 A1 | 4/2016 | Morris |
| 2017/0119491 A1 | 5/2017 | Mirsepassi |
| 2018/0338776 A1 | 11/2018 | Farley |
| 2018/0353326 A1 | 12/2018 | Hallen |
| 2019/0053825 A1 | 2/2019 | Ochoa |
| 2019/0239979 A1 | 8/2019 | Abt |
| 2019/0307527 A1 | 10/2019 | Grueebler |
| 2020/0022773 A1 | 1/2020 | Grueebler |

* cited by examiner

ADJUSTABLE LENGTH INFUSION CANNULA

PRIORITY CLAIM

This application claims the benefit of priority of U.S. Provisional Patent Application Ser. No. 62/838,612 titled "ADJUSTABLE LENGTH INFUSION CANNULA," filed on Apr. 25, 2019, whose inventor is Steven T. Charles, which is hereby incorporated by reference in its entirety as though fully and completely set forth herein.

TECHNICAL FIELD

The present disclosure relates generally to an adjustable length infusion cannula instrument.

BACKGROUND

An infusion cannula generally includes a hub and a tube-shaped cannula that can be inserted through a small incision or puncture made on a body part, often for delivery or removal of fluids. In ophthalmic surgery, an infusion cannula may be used for administration of therapeutic fluids such as saline, BSS® (Balanced Salt Solution) or air, air-gas mixtures or silicone oil to a patient's eye. For example, a surgeon makes an incision in the eye and inserts the cannula into the incision up to the hub, which acts as a stop, preventing the cannula from entering the eye completely. Fluids can be injected into the eye through the cannula Infusion cannulas used during certain procedures, such as vitrectomy, are typically 4 millimeters (mm) in length. However, for eyes with a thick choroid, using a 4 mm infusion cannula may result in a suprachoroidal or subretinal infusion of fluids in the eye. The suprachoroidal space is a potential space between the sclera and choroid that traverses the circumference of the posterior segment of the eye. The subretinal space between the photoreceptors and the retinal pigment epithelium (RPE) is the remnant of the embryonic optic vesicle. infusing fluids into the suprachoroidal or subretinal spaces may cause damage to the eye. As such, in certain cases, a 6 mm infusion cannula may be used to ensure complete passage of the cannula through the eye's thickened choroid, thereby preventing any potential suprachoroidal or subretinal infusion. However, a 6 mm infusion cannula, in some cases, obstructs a surgeon's view by blocking certain areas of the eye (e.g., peripheral retina). As such, after using the 6 mm infusion cannula for the infusion and removal of material, one solution may be for a surgeon to remove the 6 mm infusion cannula and insert a 4 mm cannula to continue the surgery without an obstructed view. However, removing and inserting cannulas in a patient's eye may not only be damaging to the eye, but it is inefficient and cumbersome.

BRIEF SUMMARY

The present disclosure relates generally to an adjustable length infusion cannula instrument.

Certain embodiments provide an adjustable length infusion cannula having an elongated cannula body including a first proximal end and a first distal end, and a hub including a second proximal end, a second distal end, and a central aperture that extends between the second proximal end and the second distal end. The central aperture is configured to accept the first distal end of the elongated cannula body and slidably advance and retract the elongated cannula body through the hub. The adjustable length infusion cannula also includes a locking mechanism positioned between the elongated cannula body and the central aperture configured to lock the cannula body within the hub such that the first distal end extends a predetermined distance past the second distal end of the hub.

Certain embodiments provide a kit for use in performing an infusion procedure, the kit including a cannula comprising a first proximal end and a first distal end, a hub comprising a second proximal end, a second distal end, and a central aperture that extends between the second proximal end and the second distal end, and a locking mechanism configured to lock the cannula within the hub such that the first distal end extends a first distance past the second distal end of the hub.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

As described below, the figures herein each illustrate an adjustable length infusion cannula that allows for adjusting the length of the cannula, thereby circumventing a need to replace infusion cannulas with different lengths. For example, each of the adjustable length cannulas described herein may be first set at a first length (6 mm). After inserting the adjustable length cannula into a patient's eye, which extends from the hub at the first length, and performing certain operations (e.g., infusing and/or removing fluids and materials) the surgeon may adjust the length of the cannula to a second length (4 mm) using the cannula's adjustment feature. Various examples of the infusion cannula instrument and its components can be made from any suitable material such as metal (e.g., stainless steel, titanium, etc.), silicone, and/or elastomeric materials (e.g., polyimide, polyvinyl chloride, polypropylene, polyethylene, polystyrene, as well as nylon, polyethylene terephthalate, polycarbonate, acrylonitrile butadiene, polyetheretherketone, polyurethane, etc.).

Figure 1A:
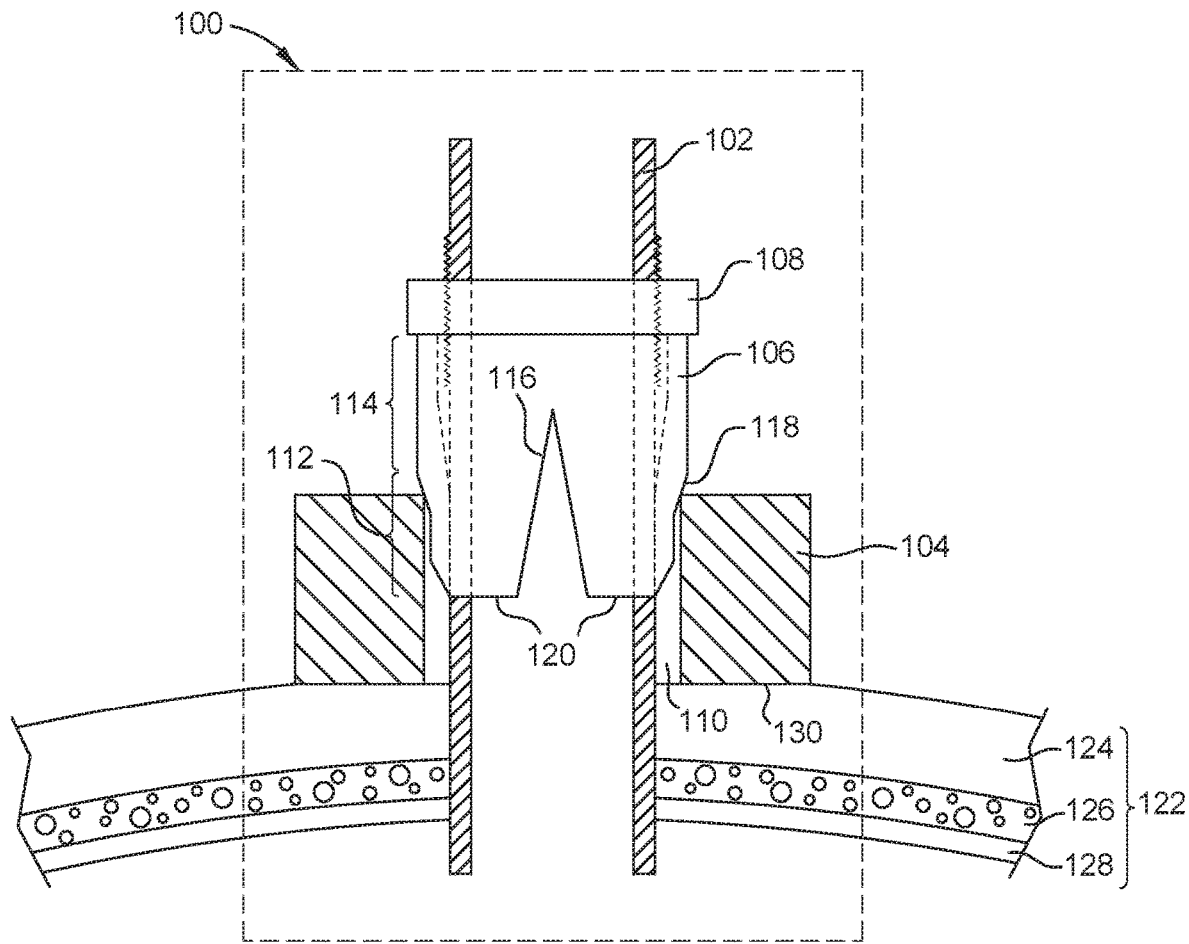
FIG. 1A illustrates a cross-sectional view of an adjustable length infusion cannula instrument in a locked state, according to some embodiments of the present disclosure.

FIG. 1A illustrates a cross-sectional view of an example adjustable length infusion cannula instrument, or "adjustable length cannula" 100 in a locked state. The adjustable length cannula 100 includes a tube-shaped cannula portion ("cannula" 102), a hub 104, a clamping element (e.g., collet 106), and a ring 108. Cannula 102 is a cylindrical, hollow tube, through which medical instruments and devices can access the interior of an eye 122. Hub 104 is generally a toroidal shape having a central aperture or central cylindrical hole 110 configured to accept the cannula 102 and allow the cannula 102 to slidably advance or retract along a longitudinal axis (i.e., upward movement and downward movement) through the hub 104. Accordingly, the diameter of cylindrical hole 110 is relatively larger than an outside diameter of cannula 102. An infusion tube or other medical instrument can be attached to the cannula 102 to facilitate infusion of fluids into the eye 122.

Collet 106 includes a gripping section 112 having a cylindrical shape configured to be received by the cylindrical hole 110. Gripping section 112 is connected to a relatively thicker and larger diameter rim section 114 by taper 118 configured to provide a gradation between the gripping section 112 and the rim section 114. Collet 106 includes one or more longitudinal separations 116 that are triangular in shape (or substantially similar) and each has an apex that terminates at rim section 114. Gripping section 112 has two separations, each located on opposite sides of the collet 106, thereby creating two collet jaws 120. Collet jaws 120 have a radially outward bias, and thus, compression of the collet jaws 120 is necessary to insert the gripping section 112 into hub 104. Due to the triangular shape, the separations 116 provide the gripping section 112 with a relatively great radial expansibility and compressibility, allowing the collet 106 compatibility with a broad range of cannula 102 diameters. It should be noted that any number of separations and/or separation shapes may be used and still be within the scope of this disclosure.

Compression of gripping section 112 is achieved by adjusting the ring 108 position along a spirally threaded section of the cannula 102 downward toward hub 104, where the ring includes a complementary threaded section paired with the threaded section of the cannula 102. Adjusting the position of ring 108 in a downward direction pushes the gripping section 112 of the collet 106 downward into cylindrical hole 110, and pushes taper 118 downward against hub 104. In response, the edges of hub 104 exert opposite force on the taper and the two collet jaws 120, causing the two collet jaws 120 to exert a positive clamping force on cannula 102. The positive clamping force of the two collet jaws 120 locks and maintains the cannula position within the collet 106 and hub 104, preventing upward and downward movement of the cannula 102.

Figure 1B:
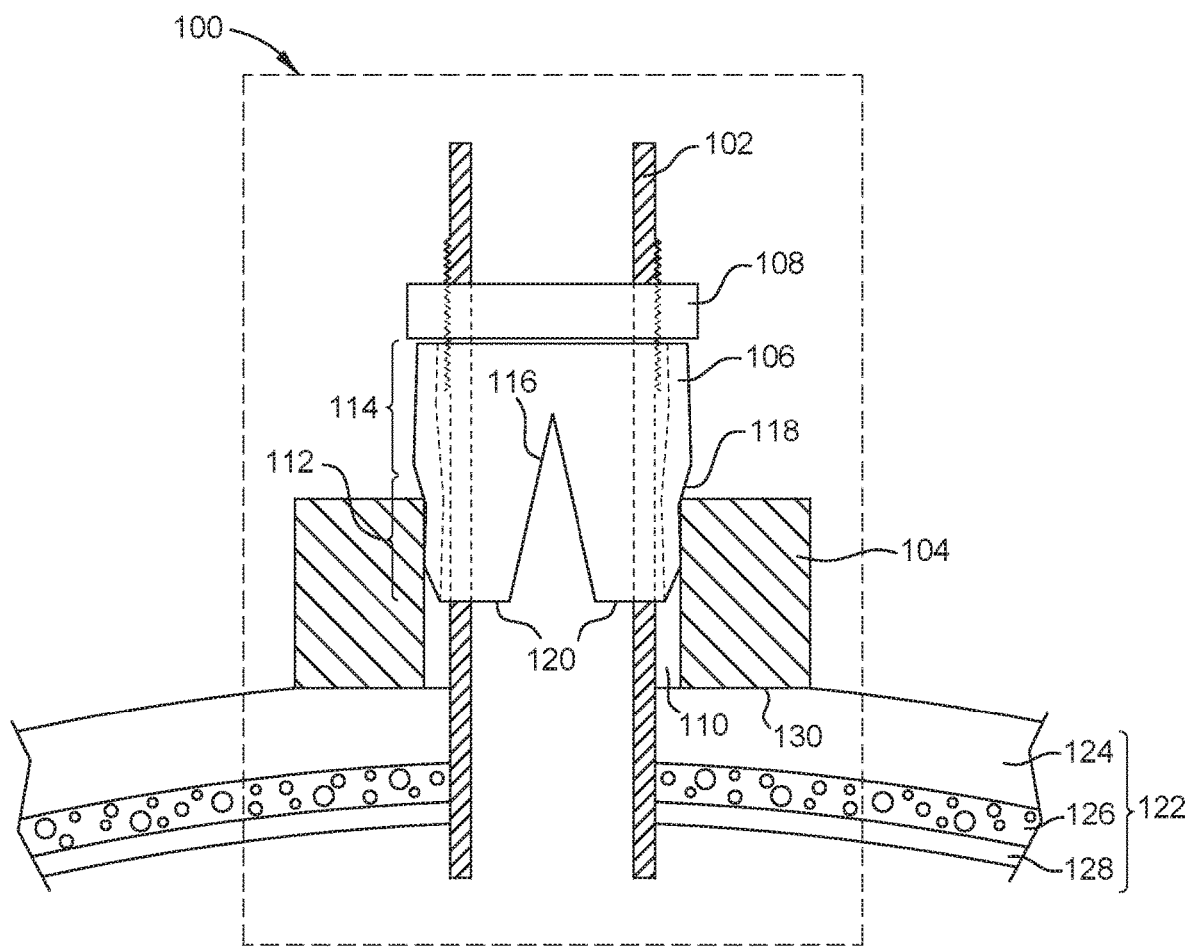
FIG. 1B illustrates a cross-sectional view of adjustable length cannula of FIG. 1A in an unlocked state, according to some embodiments of the present disclosure.

FIG. 1B illustrates a cross-sectional view of the example adjustable length cannula 100 in an unlocked state. Expansion of the gripping section 112 is achieved by adjusting the ring 108 position upward along the threaded section of the cannula 102 away from the hub 104. Adjusting the position of the ring 108 in this direction relieves the clamping force of the gripping section 112 by releasing downward pressure of the taper 118 against the hub 104. The radially outward bias of the collet jaws 120 causes the gripping section to expand, thereby pushing the taper 118 outward against the hub 104 and moving the collet 106 upward. In certain aspects, the collet 106 includes a smooth inner surface that allows the cannula 102 longitudinal movement (i.e., upward movement and downward movement) within the collet 106 and hub 104 when the collet 106 is in a released state.

In certain aspects, the adjustable length cannula 100 is initially in a locked state. That is, the cannula 102 position is locked within the collet 106 and hub 104 such that the cannula 102 extends a predetermined distance from the hub 104. In one example, the cannula 102 extends 8 millimeters (mm) (or a substantially similar length) from a base surface 130 of the hub 104. In this example, when the adjustable length cannula 100 is inserted into a patient's eye 122, the length of the cannula 102, as it extends from the hub 104, ensures the cannula 102 penetrates surface layers of the eye 122 (e.g., the sclera 124, choroid 126, etc.) to enter deeper regions (e.g., ciliary epithelium 128). Once the cannula 102 is within the desired region, a user may hand adjust the depth of the cannula 102 by adjusting the ring 108 position along the threaded section of the cannula 102.

In some embodiments, collet 106 does not include longitudinal separations 116. In such an embodiment, the gripping section 112 is formed from a soft material configured to be deformed (e.g., a soft plastic or rubber material) such that adjusting the ring 108 position downward causes the gripping section 112 to exert a positive clamping force on cannula 102 to lock and maintain the cannula position within the collet 106 and hub 104. Similarly, expansion of the gripping section 112 is achieved by adjusting the ring 108 position upward along the threaded section of the cannula 102 away from the hub 104.

Figure 2A:
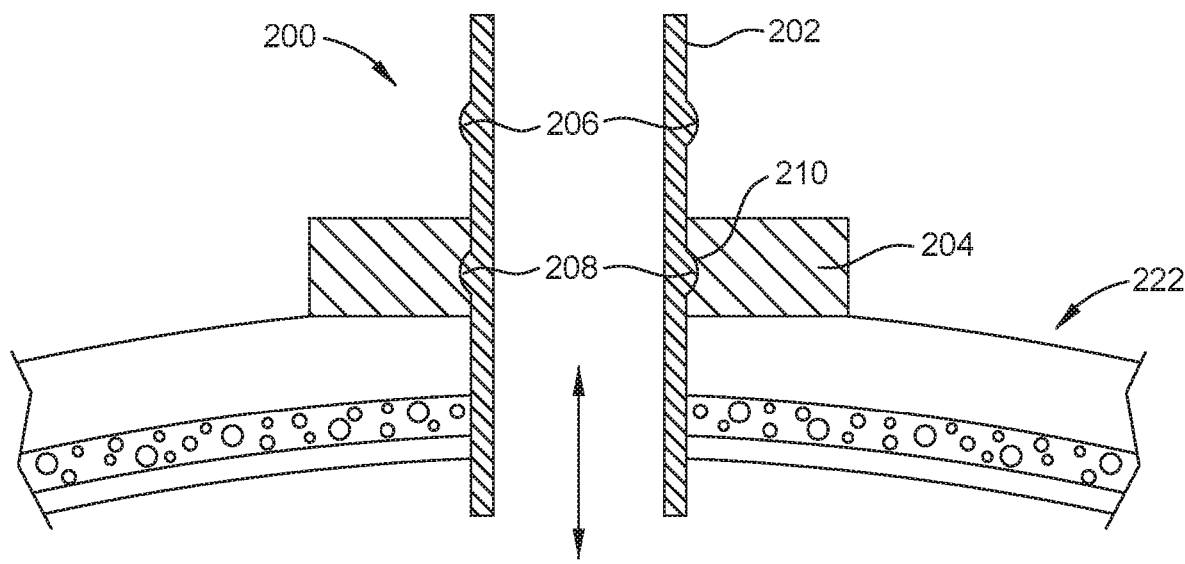
FIG. 2A illustrates a cross-sectional view of an adjustable length cannula in a first locked position, according to some embodiments of the present disclosure.

FIG. 2A illustrates a cross-sectional view of another example adjustable length cannula 200 including a cannula 202 inserted into an eye 222 and held in a first locked position within a hub 204. The cannula 202 includes a series of annularly symmetric raised rings (206 and 208) located in parallel along an outer surface of the cannula 102. The raised rings (206 and 208) extend radially outward along the circumference of the outer surface of the cannula 102. The hub 204 is generally a toroidal shape, having a cylindrical hole configured to accept the cannula 102. An inner surface of the cylindrical hole includes a groove 210 that extends annularly along the circumference of the inner surface. The groove 210 is configured to accept the rings (206 and 208) of the cannula 102 and cause a frictional lock such that the cannula 102 can be locked into multiple positions dictated by the rings (206 and 208) within the hub 204.

In certain aspects, hub 204 may be constructed of a soft plastic or rubber material to allow movement of the cannula 202 within the hub 204 to prevent sheering or other damage caused by movement between the groove 210 and the rings (206 and 208). In one example, the soft plastic material may include a polypropylene or a polyethylene polymer material. Also, in certain aspects, hub 204 may not include groove 210. In such aspects, hub 204 is constructed of a soft plastic or rubber material to allow cannula 202, having rings 206 and 208, to be inserted therein.

In some configurations, the raised rings (206 and 208) are located at positions along the cannula 202 at known lengths so that a user can adjust a depth of the cannula 202 in the eye 222. For example, a first ring 206 is positioned such that the cannula 202 extends a relatively shallow depth (e.g., 4 mm) into a patient's eye 222 when the first ring 206 is positioned within the groove 210. The second ring 206 is positioned such that the cannula 202 extends relatively deeper (e.g., 6 mm) into a patient's eye 222. As such, the user can adjust the depth of the cannula 202 to accommodate penetration of various eye layers and/or use of certain surgical instruments. It should be noted that the cannula 202 may include any number of raised rings corresponding to varying depths of the cannula 202 and be within the scope of this disclosure. In some configurations, the raised rings (206 and 208) are structural features of the cannula 202. In other configurations, the raised rings (206 and 208) are removable features such as O-rings.

Figure 2B:
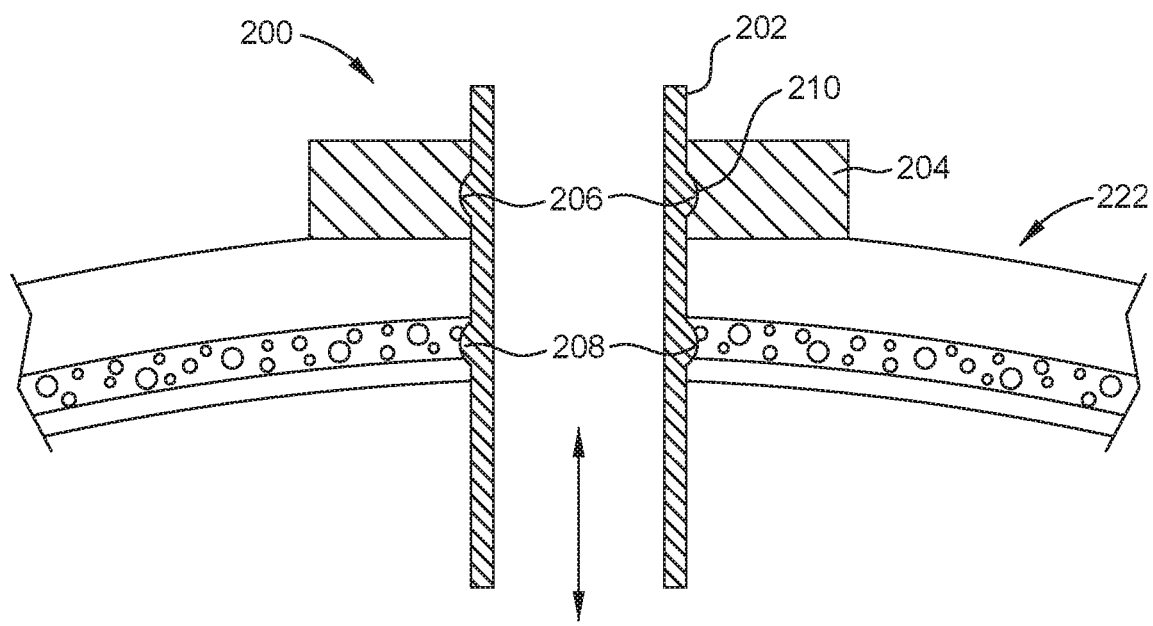
FIG. 2B illustrates a cross-sectional view of the adjustable length cannula of FIG. 2A in a second locked position, according to some embodiments of the present disclosure.

FIG. 2B illustrates a cross-sectional view of the adjustable length cannula 200 in a second locked position (i.e., the second ring 206 is positioned within the groove 210).

Figure 3A:
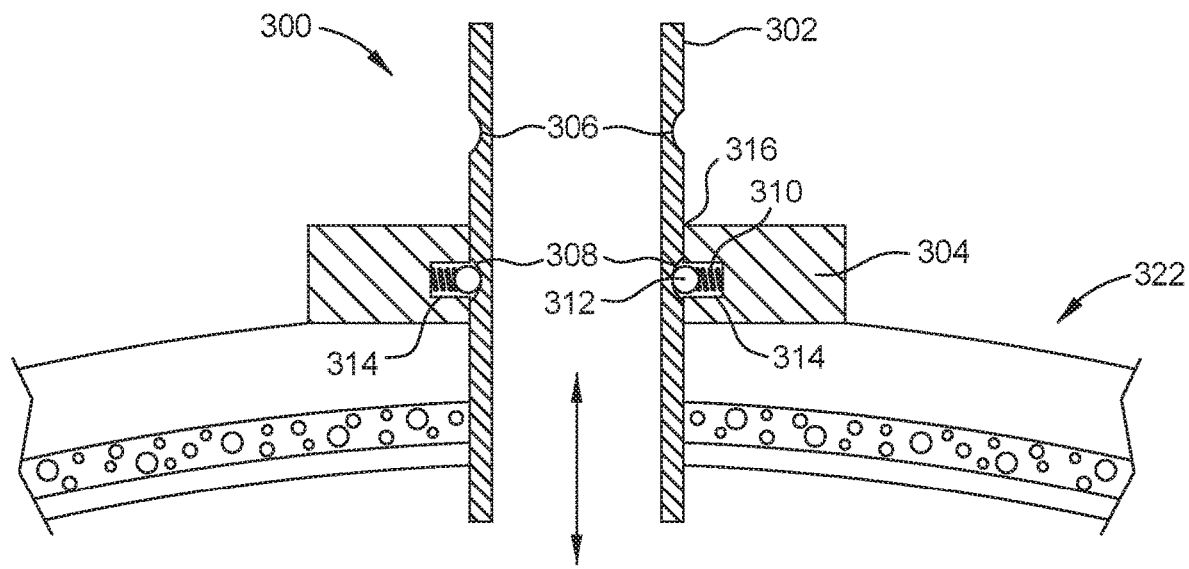
FIG. 3A illustrates a cross-sectional view of an adjustable length cannula locked in position by a spring-loaded translational detent, according to some embodiments of the present disclosure.

FIG. 3A illustrates a cross-sectional view of another example adjustable length cannula 300 including a cannula 302 inserted into an eye 322 and held in a locked position by a spring-loaded translational detent within hub 304. The cannula 302 is structured such that an outer surface includes a series of annular grooves (306 and 308). For example, a first annular groove 306 and a second annular groove 308 each form a recessed region of the outer surface of the cannula 302. Each groove is configured to accept a detent portion 312 of the hub 304. In some configurations, each annular groove (306 and 308) is characterized by a semi-circular (or substantially similar) recessed region in the outer surface of the cannula, and the detent portion 312 is a spherical shape. In various examples, the annular grooves (306 and 308) and detent portions 312 may include other suitable shapes (e.g., cylindrical, conical, etc.) for locking the cannula 302 into a position within the hub 304. In certain aspects, cannula 302 may not include grooves 306 and 308. In such aspects, cannula 302 is locked at a certain length just using the friction force that is exerted on cannula 302.

The hub 304 is generally a toroidal shape, having a central cylindrical hole configured to accept the cannula 302. An inner surface 316 of the cylindrical hole includes a plurality of cavities 314 each configured to house a detent assembly that includes the detent portion 312 and a spring 310. Each cavity 314 is configured to hold the spring 310 so that one end of the spring 310 engages the detent portion 312 and biases it outward toward the cannula 302 creating a friction lock between the detent portion 312 and the cannula 302. In some configurations, spring 310 is a compression coil spring. It should be noted however, that any other spring suitable for tension and compression may be used.

In some configurations, the annular grooves (306 and 308) are located at positions along the length of the cannula 302 indicative of a depth of cannula 302 into the eye 322. Accordingly, a user can adjust the cannula 302 position to a known depth in the eye 322. For example, the user may adjust the position of the cannula 302 within the hub 304 such that the second annular groove 308 is aligned with the plurality of cavities 314 containing the detent assemblies. Upon alignment, the bias of each spring 310 will drive the corresponding detent portion 312 into the recess of the second annular groove 308. As shown in FIG. 3A, this results in the cannula 302 being in a locked position within the hub 304. In some configurations, the second annular groove 308 is positioned such that the cannula 302 extends a relatively shallow depth (e.g., 4 mm) into the eye 322. Accordingly, the cannula 302 extends 4 mm into the eye 322 in the first locked position. The first annular groove 306 is positioned such that the cannula 302 extends relatively deeper (e.g., 6 mm) into a patient's eye 322 in a second locked position. Accordingly, the user can adjust the depth of the cannula 302 to accommodate penetration of various eye layers and/or use of particular surgical instruments. It should be noted that the cannula 302 may include any number of annular grooves corresponding to varying depths of the cannula 302.

Figure 3B:
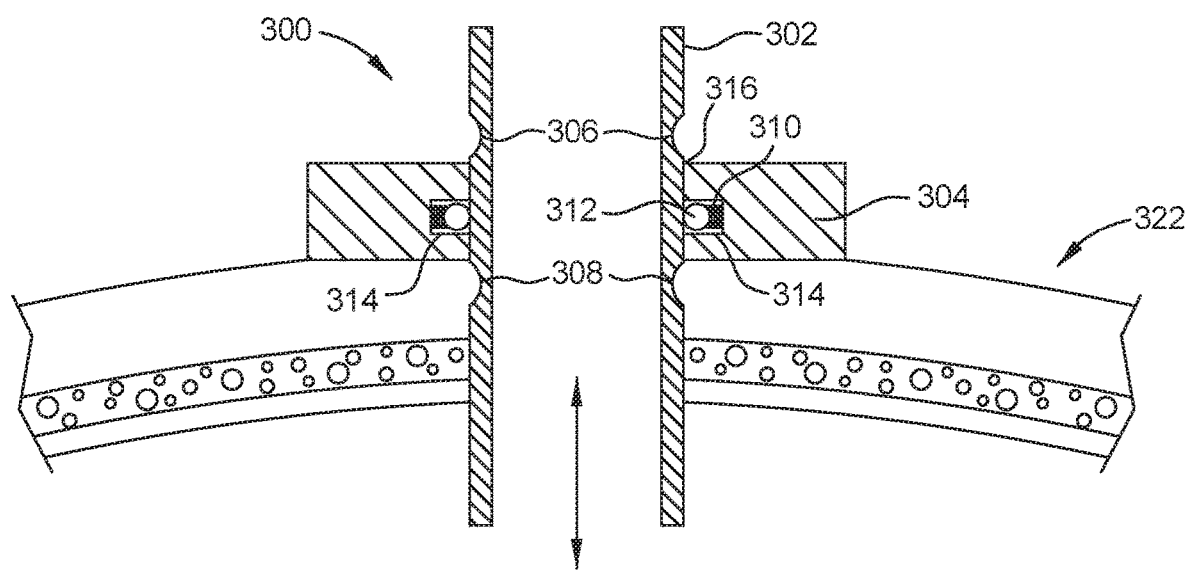
FIG. 3B illustrates a cross-sectional view of the adjustable length cannula of FIG. 3A in an unlocked position, according to some embodiments of the present disclosure.

FIG. 3B illustrates a cross-sectional view of the adjustable length cannula 300 in a position between the first locked position and the second locked position. Although the detent portions 312 are not resting in an annular groove (306 and 308) of the cannula 302, the friction between the detent portion 312 and the cannula 302 caused by the spring holds the cannula 302 in a movably durable position. Accordingly, in some embodiments, the cannula 302 can have a smooth outer surface without the annular grooves (306 and 308) illustrated in FIGS. 3A and 3B.

Figure 4A:
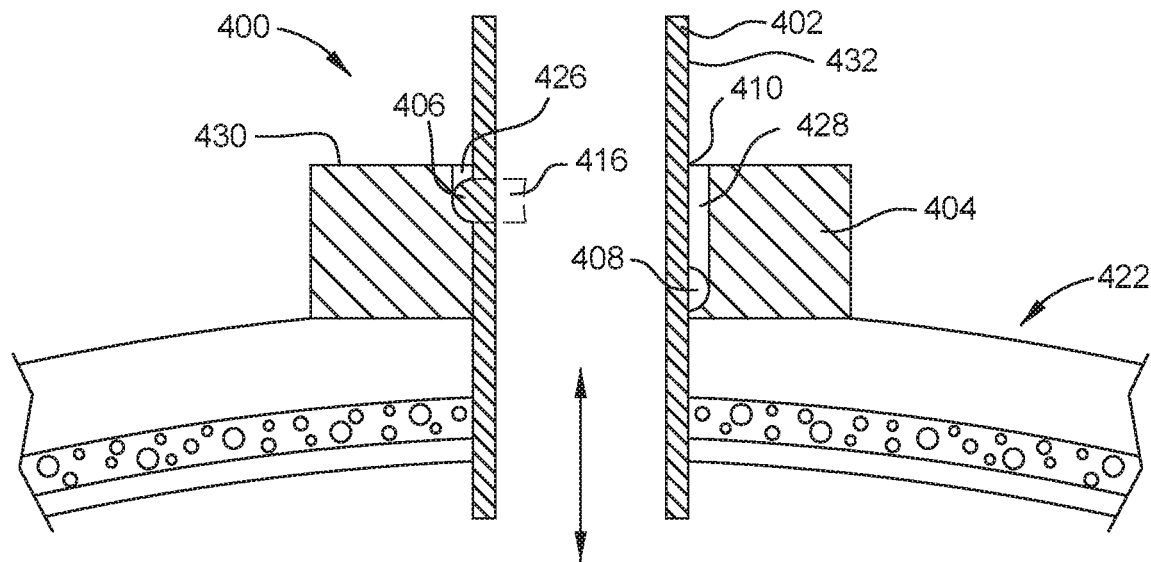
FIG. 4A illustrates a cross-sectional view of an adjustable length cannula in a first locked position, according to some embodiments of the present disclosure.

FIG. 4A illustrates a cross-sectional view of another example adjustable length cannula 400 in a first locked position. The adjustable length cannula 400 includes a cannula 402 inserted through a hub 404 via a cylindrical hole 434 in the center of the hub 404, and into an eye 422. An exterior surface 432 of the cannula 402 is structured such that it includes a raised portion 406. The hub 404 includes a first recessed opening 426 and a second recessed opening 428 formed in the top surface 430 of the hub 404. The first recessed opening 426 and the second recessed opening 428 each provide entry to a corresponding vertical portion of a grooved channel in an inner surface 410 of the hub 104.

Accordingly, the first recessed opening 426 and the second recessed opening 428 are configured to accept the raised portion 406 such that the cannula 402 can be moved downward along the vertical portion of the grooved channel within the hub 104. Each recessed opening (426 and 428) is configured to direct the raised portion 406, via the vertical groove, into one of a first locking cavity 416 or a second locking cavity 408 formed in the inner surface 410 of the cylindrical hole 434. Each of the first locking cavity 416 and the second locking cavity 408 form a horizontal portion of the grooved channel, each having a particular length that extends semi-annularly along the inner surface 410 of the hub. In one example, each of the first locking cavity 406 and the second locking cavity 408 extends a quarter of the circumference of the inner surface 410, although other suitable lengths are contemplated. Each of the first locking cavity 416 and the second locking cavity 408 are configured to accept the raised portion 406 of the cannula 402 from one of the vertical portions of the grooved channel, and compress the raised portion within the locking cavities (416 and 418), thereby locking the cannula 402 within the hub 404 to prevent vertical movement of cannula 402.

For example, a user may insert the cannula 402 into the hub 404 such that the raised portion 406 is accepted into the first recessed opening 426. The user may then twist or rotate the cannula 402 (e.g., in a clockwise manner) to move the raised portion 406 into the first locking cavity 416. Similarly, the user may insert the cannula 402 into the hub 404 such that the raised portion 406 is accepted into the second recessed opening 428, then rotate the cannula 402 to move the raised portion 406 into the second locking cavity 408. Accordingly, once the raised portion 406 of the cannula 402 is positioned within one of the first locking cavity 416 or the second locking cavity 408, the cannula 402 is prevented from sliding up or down within the hub 404. As such, the cannula 402 is locked within the hub 404 to provide for a specific depth of the cannula 402 within the eye 422. For example, if the raised portion 406 of the cannula 402 is positioned within the first locking cavity 416, the cannula 402 extends to a depth of 4 mm into the eye 422. In another example, if the raised portion 406 of the cannula 402 is positioned within the second locking cavity 408, then the cannula 402 extends a depth of 6 mm into the eye 422.

Figure 4B:
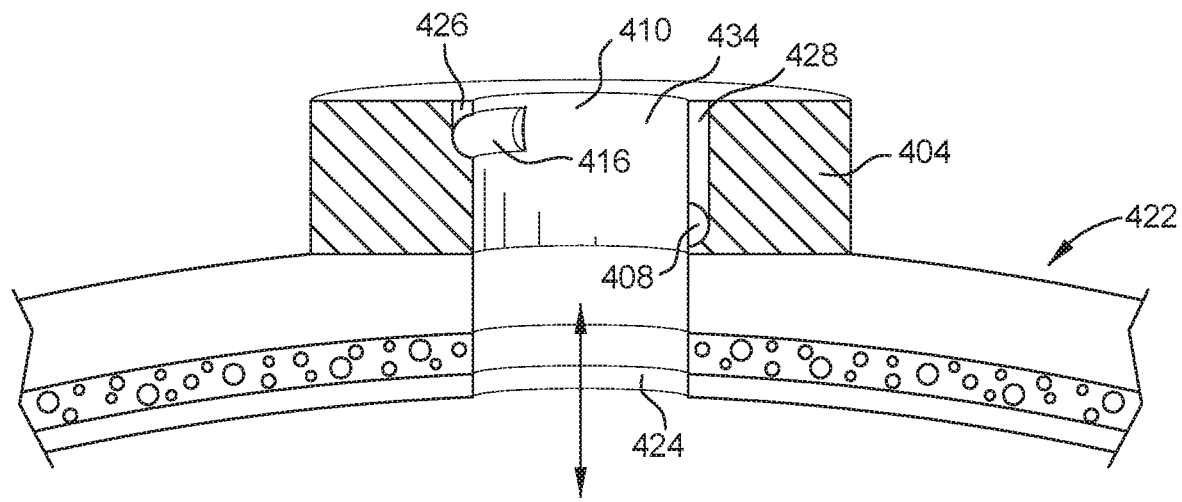
FIG. 4B illustrates a cross-sectional and top-center perspective view of the hub of FIG. 4A, according to some embodiments of the present disclosure.

The user may remove the cannula 402 from the hub 404 by rotating the cannula 402 until the raised portion 406 reaches the corresponding recessed opening (426 or 428). From this point, the user can extract the cannula 402 from the hub 404, and in some cases, insert another cannula portion as needed. FIG. 4B illustrates a cross-sectional view of the hub 404 positioned over an incision 424 or puncture of the eye 422 with the cannula 402 removed. The incision 424 provides a means by which the cannula 402 can be inserted into the eye 422.

Figure 5:
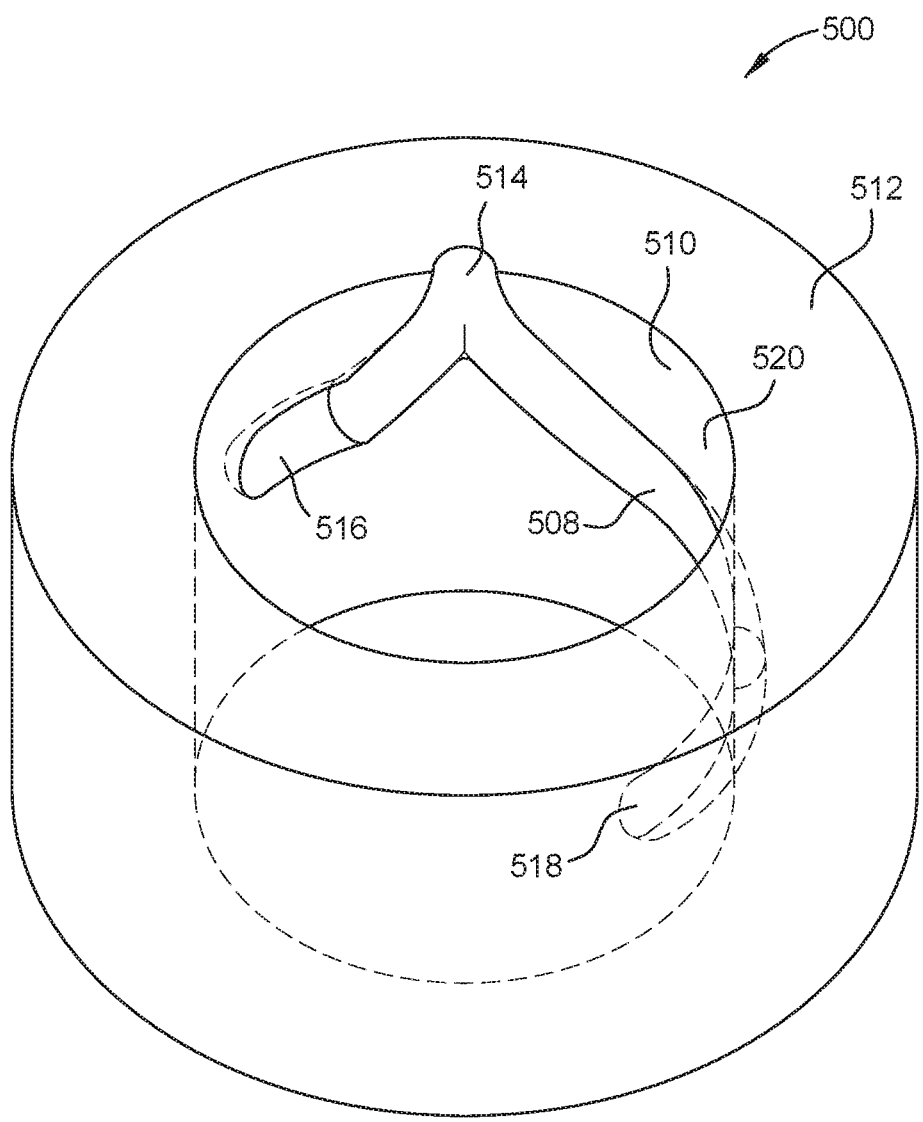
FIG. 5 illustrates a top-center perspective view of an alternative embodiment of a hub configured to be used with the cannula illustrated in FIGS. 4A and 4B.

FIG. 5 illustrates a top-center perspective view of an alternative embodiment of a hub 500 configured to be used with the cannula 402 of FIGS. 4A and 4B. Here, a path formed by a grooved channel 508 shown along an inner surface 520 of a cylindrical hole 510 through the center of the hub 500. The grooved channel 508 includes a first locking cavity 516, a second locking cavity 518, and a recessed opening 514.

In some configurations, the cannula 402 can be inserted into the cylindrical hole 510 of the hub 500, and rotated such that the raised portion 406 of the cannula 402 is positioned above a recessed opening 514. The recessed opening 514 is configured to accept the raised portion 406 of the cannula 402 through an opening in a top surface 512 of the hub. Once the raised portion 406 is accepted through the recessed opening 514, the raised portion 406 can move along the path created by the grooved channel 508. Accordingly, the grooved channel 508 provides a fixed path or channel configured to guide the raised portion 406 into various positions (e.g., first locked position, second locked position) corresponding to various depths of cannula 402 within the eye 422.

Once the cannula 402 is inserted into the hub 500, and the raised portion is accepted into the path created by the grooved channel 508, a user may twist or rotate the cannula 402 to move the raised portion 406 into different positions along the grooved channel 508. For example, the user may lock the cannula 402 into the first locked position by rotating the raised portion 406 counter-clockwise into a first locking cavity 516. Similarly, the user may lock the cannula 402 into the second locked position by rotating the raised portion 406 clockwise into a second locking cavity 518. The user may remove the cannula 402 from the hub 500 by rotating the cannula 402 until the raised portion 406 reaches the channel opening 514. From this point, the user can extract the cannula 402 from the hub 500, and in some cases, insert another cannula portion as needed.

The first locking cavity 516 and the second locking cavity 518 are illustrated as extreme ends of the grooved channel 508. This provides the benefit of locking the cannula 402 into a position and preventing the user from inadvertently moving the raised portion past that position. In some configurations, the first locking cavity 516 and the second locking cavity 518 have a shallower depth than the depth of the remaining portions of the grooved channel 508. Accordingly, the shallower depth of the locking cavities (516 and 518) will enable a friction lock between the raised portion 406 and the locking cavities. In some configurations, the top of the interior surface of the locking cavities and/or the raised portion may include a series of ridges or other pattern of tread (e.g., interlocking saw-tooth pattern, tongue-and-groove pattern, etc.) configured to increase the effectivity of the friction lock.

Figure 6A:
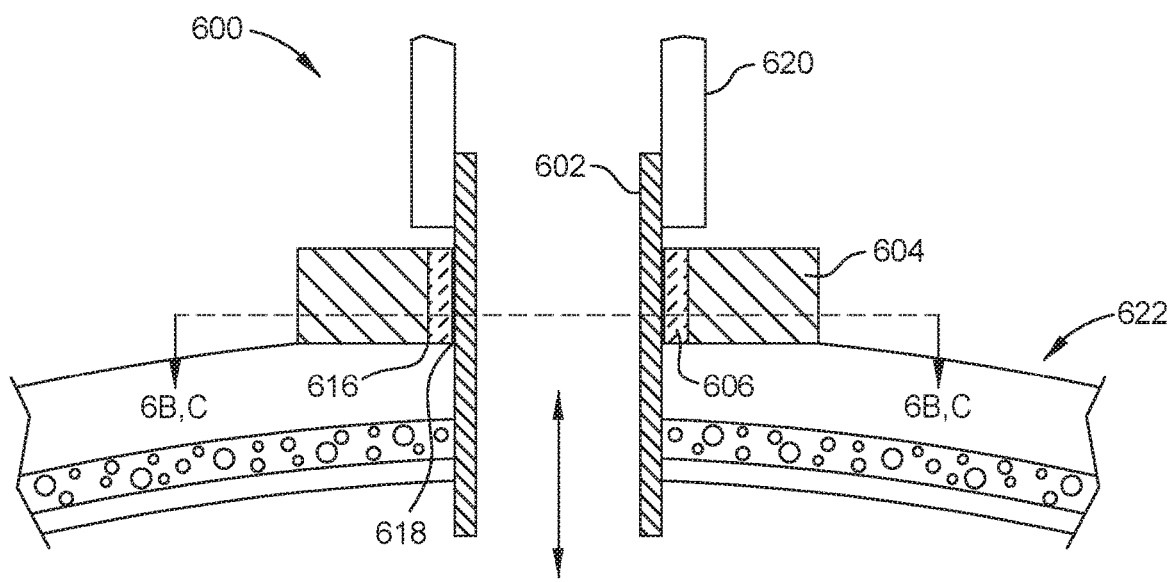
FIG. 6A illustrates a cross-sectional view of an adjustable length cannula, according to some embodiments of the present disclosure.

FIG. 6A illustrates a cross-sectional view of another example adjustable length cannula 600 including a hub 604 holding a cannula 602 inserted in an eye 622. The hub 604 includes an inner surface 616 defining a central cylindrical hole 610 that is configured to include a lining (e.g., an eyelet or grommet 606) made up of a soft plastic or rubber material. The grommet 606 is positioned within the cylindrical hole 610 and includes a circular hole 618 configured to accept the cannula 602. Accordingly, the grommet 606 is positioned between the inner surface 616 and the cannula 602.

Figure 6B:
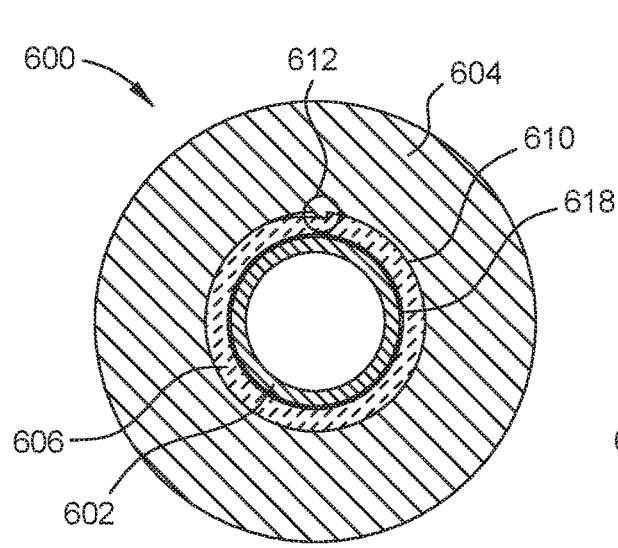
FIG. 6B illustrates a top view of the adjustable length cannula of FIG. 6A in an unlocked position, according to some embodiments of the present disclosure.

FIG. 6B illustrates a top view of the adjustable length cannula 600 showing the hub 604 in an unlocked position. The hub 604 includes a raised saw-tooth portion 612 that extends outward from the inner surface 616 into a complementary saw-tooth cavity 614 (see FIG. 6C below) of the grommet 606. The saw-tooth cavity 614 is configured to receive the saw-tooth portion 612 from one direction. It should be noted that the outside diameter of the cannula 602 is slightly smaller than the inside diameter of the grommet 606, thereby allowing a user to move the cannula 602 and adjust its depth while the hub 604 is in an unlocked position.

Figure 6C:
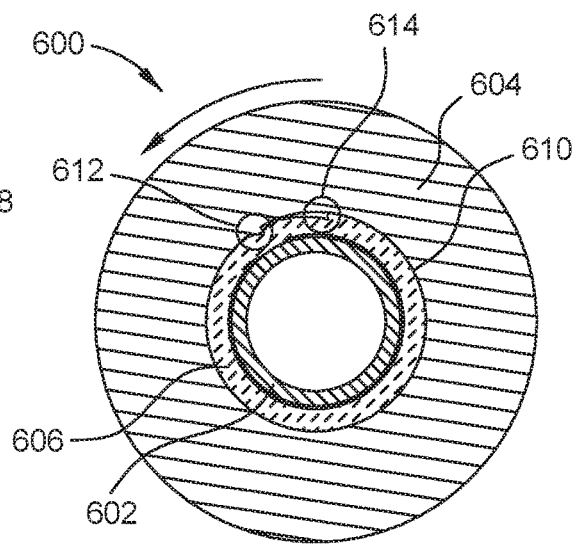
FIG. 6C illustrates another top view of the adjustable length cannula of FIG. 6A in a locked position, according to some embodiments of the present disclosure.

FIG. 6C illustrates a top view of the adjustable length cannula 600 showing the hub 604 in a locked position. In this example, the saw-tooth portion 612 is positioned outside of the saw-tooth cavity 614, and is thus exerting pressure on a surface of the grommet 606. This in turn distorts the circular hole 618 that contains the cannula 602 and creates a frictional lock that holds the position of the cannula 602 within the hub 604.

Accordingly, the user can unlock and adjust the position of the cannula 602 by rotating the hub 604 about the grommet 606 such that the saw-tooth protrusion 612 is received by the saw-tooth cavity 614. In some configurations, the grommet 606 is held in place by the cannula 602 while the hub 604 is rotated. In another configuration, the grommet 606 is held in place by an apparatus 620 attached to the cannula 602. For example, the apparatus 620 may include an infusion tube or medical instrument that can be attached to the cannula 602 to facilitate infusion of fluids into the eye 622.

The user may lock the position of the cannula 602 within the hub 604 by rotating the hub 604 about the grommet 606 such that the saw-tooth protrusion is gradually removed from the saw-tooth cavity 614 and a gradual pressure is applied to the cannula 602 from the distorted shape of the circular hole 618. It should be noted that the grommet can be removed and replaced with a differently sized grommet to accommodate a cannula portion having a different length.

The foregoing description is provided to enable any person skilled in the art to practice the various embodiments described herein. Note that, herein, a distal end of a component refers to the end that is closer to a patient's body. On the other hand, the proximal end of the component refers to the end that is facing away from the patient's body. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An adjustable length infusion cannula, comprising:
   a cannula comprising a first proximal end and a first distal end;
   a hub comprising a second proximal end, a second distal end, and a central aperture that extends between the second proximal end and the second distal end, wherein the central aperture is configured to accept the first distal end of the cannula and allow the cannula upward movement and downward movement through the hub; and
   a locking mechanism configured to:
     lock the cannula within the hub such that the first distal end of the cannula extends a first distance past the second distal end of the hub, and
     lock the cannula within the hub such that the first distal end of the cannula extends a second distance past the second distal end of the hub after a position of the cannula is adjusted through the hub;
   wherein the locking mechanism comprises a clamping element positioned in the central aperture between the cannula and the hub;
   wherein the cannula comprises a spiral threaded element along an outer surface of the cannula, wherein the spiral threaded element is configured to accept a ring having a complementary threaded element;
   wherein the ring is configured for upward and downward movement along a longitudinal axis between the first proximal end and a first distal end of the cannula. and
   wherein downward ring movement is configured to lock the cannula within the hub via the clamping element.

2. The adjustable length infusion cannula of claim 1, wherein locking the cannula within the hub prevents the upward movement and the downward movement of the cannula.

* * * * *